United States Patent [19]

Plüss

[11] Patent Number: 5,445,605
[45] Date of Patent: Aug. 29, 1995

[54] TAMPON WITH HOLDER

[76] Inventor: Bruno Plüss, Schwalbenweg 10, CH-4310 Rheinfelden, Switzerland

[21] Appl. No.: 176,462

[22] Filed: Jan. 3, 1994

[30] Foreign Application Priority Data

Jan. 5, 1993 [CH] Switzerland .................. 22/93

[51] Int. Cl.$^6$ ............................................. A61F 13/20
[52] U.S. Cl. ............................................. 604/13; 604/11; 604/14; 604/904
[58] Field of Search ....................... 604/11-18, 604/904

[56] References Cited

U.S. PATENT DOCUMENTS

| | | | |
|---|---|---|---|
| 2,355,917 | 8/1944 | Knight | 604/11 |
| 3,998,225 | 12/1976 | Hytonen | 604/11 |
| 4,900,299 | 2/1990 | Webb | 604/11 |
| 5,135,475 | 8/1992 | Nakanishi et al. | 604/904 |

FOREIGN PATENT DOCUMENTS 2523337 12/1975 Germany .................. 604/15
2097259A 11/1982 United Kingdom .

Primary Examiner—Randall L. Green
Assistant Examiner—P. Zuttarelli
Attorney, Agent, or Firm—Spencer, Frank & Schneider

[57] ABSTRACT

A holder for a tampon having a withdrawing thread. The holder has a rigid, cylindrical sheath encasing the tampon. The sheath has a tampon expulsion opening, an expulsion end region, and another end region, respectively. The expulsion end region has a hole therethrough for accommodating and guiding the withdrawing thread. The hole is proximate to the expulsion opening. The another end region has more than one notch. The tampon is partially expulsed out of the sheath through the expulsion opening by pulling on the withdrawal thread.

3 Claims, 1 Drawing Sheet

TAMPON WITH HOLDER

BACKGROUND OF THE INVENTION

This invention concerns a tampon provided with a holder, intended for insertion into the vagina. There is a prior art tampon/holder combination of this type, where the holder is designed as a rigid, cylindrical sheath which encases the tampon and the tampon is provided with a withdrawing thread which is guided out of the sheath in such a way that the tampon can be partially pushed out of the sheath by pulling on the thread. In this form of prior art embodiment the sheath encasing the tampon and serving as the holder is somewhat, i.e. for example, 30–60%, longer than the tampon, so that the tampon housed within is well protected. At the front end of the sheath, i.e. at the expulsion end, there is a 7–13 mm deep notch. One end of the tampon, the front end which is inserted into the vagina, does not finish bluntly, but is somewhat tapered, semispherically, for example, whilst the opposite end, i.e. the back end is flat. The withdrawing thread is affixed to this back end. It is guided away from the back end of the tampon and along the tampon to the notch at the front end of the sheath, at which point it exits the sheath, so that the tampon can be pushed out of the sheath by pulling on this thread. The notch is to ensure that when the thread is pulled towards the back end of the sheath, the end of the tampon whose length corresponds to the length of the notch remains in the sheath, so that the latter serves as a holder for insertion into the vagina.

However, this form of embodiment does have various, not insignificant disadvantages: on the one hand, the rigidity of the sheath is reduced by the notch, so that the thickness of its wall has to be greater than would be necessary for a sheath without a notch. On the other hand, if the thread is not pulled carefully, namely, if the pulling action is not carefully directed towards the back end of the sheath, the tampon is pulled entirely out of the sheath, so that it has to be reinserted with difficulty, and when the tampon is introduced into the vagina the thread must in addition be laboriously held tightly so that the tampon is not pushed back into the sheath. Furthermore, when inserted into the vagina, the ends of the notches at the front can cause injuries.

SUMMARY OF THE INVENTION

This new combination of tampon and sheath now serves to overcome all these disadvantages, the sheath differing from the prior art sheath in that on the one hand, it has a hole close to the end out of which the tampon is to be expulsed, through which the thread is guided outwards, and in that on the other hand, there are two notches at the other end, and its outer surface is preferably provided with a concentrically running rib.

An example of an embodiment of the invention will be described below, with reference to the accompanying drawing, in which:

DETAILED DESCRIPTION OF THE INVENTION

Figure 1:
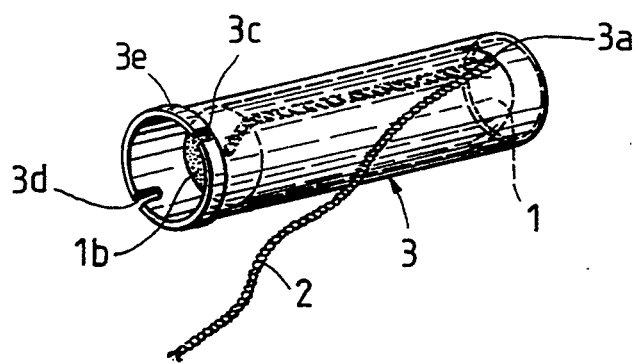
FIG. 1 shows a tampon housed in the sheath, i.e. as it will be available for purchase, although the protective covering which is usually provided for hygienic reasons is omitted, whilst

The tampon designated as a whole by 1 has a rounded front end 1a and a flat back end 1b. The withdrawing thread 2 is affixed at the centre of this back concluding surface 1b. The tampon lodges approximately in the centre of a rigid, cylindrical sheath 3 preferably made of plastic or a biodegradable material (such as e.g. starch), which is ca. 30% to 60% longer than the tampon 1 and the dimensions of its diameter being such that the tampon which is per se somewhat elastic cannot simply slip out, but can be extracted without using too much force, as is known from the relevant literature.

Figure 2:
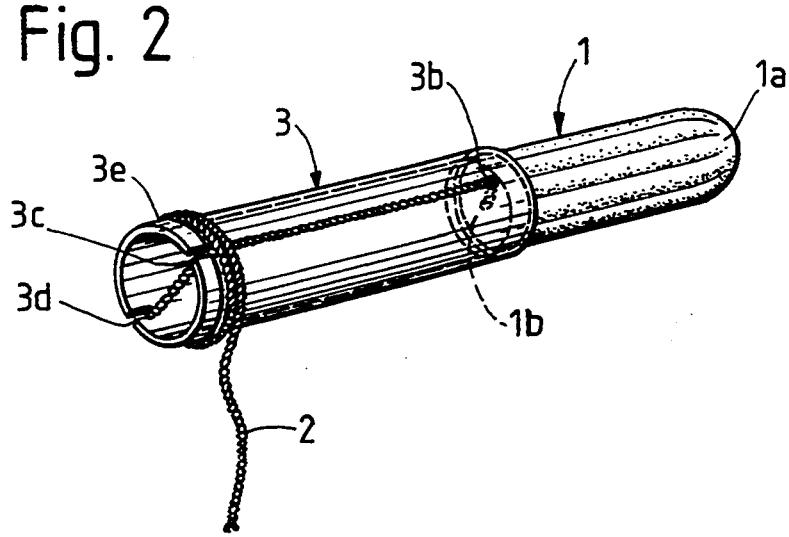
FIG. 2 shows the device consisting of sheath and tampon in the position adapted for inserting the tampon into the vagina.

The special design of the sheath 3 is new: close to the expulsion end 3a there is a hole 3b, through which the withdrawing thread 2 is guided. At the other end there are two notches, grooves or incisions 3c and 3d, and a concentrically running rib 3e. It is particularly useful if the expulsion end of the sheath is slightly conically narrowed, although tis can scarcely be perceived in the drawing. When the tampon is to be inserted into the vagina, it is brought from the position shown in FIG. 1 into the position shown in FIG. 2 by pulling on the thread 2. However, since there is a hole 3b close to the expulsion end of the sheath 3 at a distance of ca. 5–12 mm from this end, through which the thread 2 is guided outwards, it is impossible to pull the tampon completely out of the sheath by pulling on the thread. The back end of the tampon thus remains lodged in the sheath 3, without it being necessary to pay particular attention to the direction of the pulling action. If, as is the case in a preferred form of embodiment, the front end of the sheath is tapered very slightly, the tampon is sure to sit sufficiently securely even when lodged in the sheath with only its 5–10 mm long end. Furthermore, the tampon is held securely in the position shown in FIG. 2 through every pull on the thread 2. Nor is there any possibility of causing injury on insertion since there are no notches at the expulsion end of the sheath.

The two notches 3c and 3d serve in conjunction with the concentrically running rib 3e to hold the thread 2 without any problem, thus ensuring that tampon and holder remain securely connected when inserting the tampon into the vagina. As clearly illustrated in FIG. 2, after the tampon has been expulsed from the sheath 3 by pulling on the thread 2, the free end of the thread 2 is placed in the two notches 3c and 3d and then guided around the sheath at least once, the rib serving to prevent the thread from slipping. When the sheath is held, the thread is thus also held securely without any particular attention having to be paid, and the tampon can therefore be reliably inserted into the vagina without any problem. After inserting the tampon the thread can be released and the sheath removed, whilst the tampon remains in the vagina.

What is claimed is:

1. A holder for a tampon having a withdrawing thread attached at one end, said holder comprising:
   a rigid, cylindrical sheath for encasing a tampon and having one open end through which the tampon can be expulsed from said sheath and an opposite end provided with notches, said sheath having a hole near said one open end through which the withdrawing thread of the tampon is passed wherein by pulling the thread through the hole the tampon can be guided through said one open end to a partially expulsed position and secured temporarily in the partially expulsed position by pulling the withdrawing thread through said notches.

2. The holder of claim 1, wherein said sheath is conically narrowed toward said one open end from which the tampon is expulsed.

3. The holder of claim 1, wherein the withdrawing thread may be wrapped around said sheath to facilitate holding the withdrawing thread in said notches, and said sheath has an outer surface and includes a concentrically running rib on said outer surface adjacent said opposite end to serve as an abutment to prevent the thread from slipping off the opposite end of said sheath when the thread is wrapped around said sheath.

* * * * *